US00PP09963P

United States Patent [19]

Bradford et al.

[11] Patent Number: Plant 9,963

[45] Date of Patent: Jul. 15, 1997

[54] NECTARINE TREE "RUBY SWEET"

[76] Inventors: Lowell Glen Bradford, 12439 E. Savana Rd.; Norman G. Bradford, 11875 E. Savana Rd., both of Le Grand, Calif. 95333

[21] Appl. No.: 654,090

[22] Filed: May 28, 1996

[51] Int. Cl.[6] ..... A01H 5/00

[52] U.S. Cl. ..... Plt./41.1

[58] Field of Search ..... Plt./41.1

[56] References Cited

U.S. PATENT DOCUMENTS

P.P. 7,507 4/1991 Bradford et al. ..... Plt./41

P.P. 9,360 11/1995 Bradford et al. ..... Plt./40.1

*Primary Examiner*—James R. Feyrer

[57] ABSTRACT

The present invention relates to a nectarine *Prumus persica* tree and more particularly to a new and distinct variety broadly characterized by a medium size, vigorous, hardy, productive and regular bearing tree. The fruit matures under the ecological conditions described approximately the last week in June, with first picking on Jun. 26, 1995. The fruit is uniformly medium to large in size, subacidic in flavor, attractively globose in shape, clingstone in type, very firm in texture, and full red in skin color. The variety was developed as a fruit generation hybridization using Spring Bright (U.S. Plant Pat. No. 7,507) as the selected seed parent and June Pearl Nectarine (U.S. Plant Pat. No. 9,360) as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Ruby Sweet". The present variety was hybridized in 1992 by us in a cultivated area of our experimental orchard at Bradford Farms near Le Grand, Calif. in Merced County (San Joaquin Valley). It was the result of a first generation cross using Spring Bright (U.S. Plant Pat. No. 7,507) yellow flesh nectarine as the selected seed parent and June Pearl (U.S. Plant Pat. No. 9,360) white flesh nectarine as the selected pollen parent. Subsequent to origination of the present variety of nectarine tree, we asexually reproduced it by budding and grafting, and such reproduction of plant and fruit characteristics were true to the original plant in all respects.

The present variety is most similar to its seed parent, the Spring Bright Nectarine (U.S. Plant Pat. No. 7,507), by producing fruit that is large in size, very firm in texture, clingstone in type, and full red in skin color, but is distinguished therefrom and an improvement thereon by blooming 1 week later, having reniform glands instead of globose, having a bitter kernel instead of sweet, and by producing fruit that matures 7 days later and is subacidic in flavor instead of acidic.

The present variety is similar to its pollen parent, the June Pearl (U.S. Plant Pat. No. 9,360), by producing clingstone fruit that is full red in skin color and subacidic in flavor, but is very distinguished therefrom by producing fruit that is yellow in flesh color instead of white and that matures about 16 days later.

DRAWING

The accompanying photograph exhibits four whole fruits positioned to display the characteristics of the skin color and form, a sectioned half fruit divided transverse to the suture plane to reveal the flesh, a typical stone, and representative leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Jun. 28, 1995. All major color code designations are by reference to the Inter-Society Color Council, National Bureau of Standards. Common color names are also used occasionally.

TREE

Size:l Medium.
Vigor: Vigorous.
Growth: Upright and dense.
Form: Vase formed.
Hardiness: Hardy.
Production: Productive.
Bearing: Regular bearer.
Trunk:
- *Size.*—Medium.
- *Texture.*—Medium.
- *Bark color.*—Grayish yellowish brown [80. gy.yBr].
- *Lenticels.*—Numerous. Color: Dark yellowish brown [78. d.yBr]. Average size: ¼" [6.4 mm.].

Branches:
- *Size.*—Medium.
- *Texture.*—Medium.
- *Color.*—1st year wood topside: Grayish red [19. gy.R]. 1st year wood underside: Brilliant yellow green [116. brill.YG]. Older wood: Moderate brown [58. m.Br].
- *Lenticels.*—Numerous, very small. Color: Strong yellowish brown [74. s.yBr]. Average size: 1/16" [1.6 mm.].

Leaves:
- *Size.*—Medium. Average length: 5½" [139.7 mm.]. Average width: 1⅝" [41.3 mm.].
- *Thickness.*—Medium.
- *Form.*—Elliptical.
- *Apex.*—Acuminate.
- *Base.*—Acute.
- *Surface.*—Smooth.

*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: 7/16" [11.1 mm.]. Average thickness: 1/16" [1.6 mm.]. Color: Moderate yellow green [120. m.YG].
*Stipules.*—Numerous. Average length: ¼" [6.4 mm.].
*Glands.*—Average number: 2–4 per leaf. Position: Alternately positioned on petiole and base of blade. Size: Medium. Form: Reniform. Color: Moderate yellow green [120. m.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium as compared with other varieties.
*Size.*—Large.
*Color.*—Light purplish pink [249. l.pPk].

FRUIT

Maturity when described: Hard eating ripe, Jun. 28, 1995.
Date of first picking: Jun. 26, 1995.
Date of last picking: Jul. 5, 1995.
Size: Uniform, medium.
*Average diameter axially.*—2⅝" [66.7 mm.].
*Average transversely in suture plane.*—2¾" [69.9 mm.].
Form: Uniform, globose, symmetrical, slightly compressed toward the suture.
*Longitudinal section form.*—Circular.
*Transverse section through diameter.*—Circular to elliptical.
Suture: An inconspicuous line extending from the base to beyond the apex, having a slight depression beyond the pistil point.
Ventral surface: Rounded, lipped toward the apex on both sides.
Lips: Slightly unequal.
Cavity: Flaring, circular to slightly elongated in the suture plane, suture showing on both sides, stem markings present.
*Depth.*—½" [12.7 mm.].
*Breadth.*—⅞" [22.2 mm.].
Base: Rounded to truncate.
Apex: Rounded.
Pistil point: Negligible in length, apical, depressed within the suture.
Stem: Medium.
*Average length.*—⅜" [9.5 mm.].
*Average width.*—3/16" [4.8 mm.].
Skin:
*Thickness.*—Medium.
*Texture.*—Medium.
*Tenacity.*—Tenacious to flesh.
*Tendency to crack.*—Slight in the wet season.
*Color.*—Dark red [16. d.R] blending into a strong reddish orange [35. s.rO] background, with moderate orange yellow [71. m.OY] freckling toward the apex.

Flesh:
*Color.*—Brilliant yellow [83. brill.Y] with a very minot amount of moderate red [15. m.R] streaking very close to the pit on more mature fruits.
*Amygdalin.*—Scarce.
*Juice.*—Abundant, rich.
*Texture.*—Firm, crisp.
*Fibers.*—Abundant, fine.
*Ripens.*—Slightly earliest at the apex.
*Flavor.*—Mild sweet subacidic with 15 brix.
*Aroma.*—Moderate.
*Eating quality.*—Very good.

STONE

Type: Clingstone.
Form: Oval.
Base: Oblique.
Apex: Acute to acuminate.
Sides: Equal.
Surface: Pitted over most of the surface, a few irregular horizontal furrows toward the apex.
Ridges: Jagged toward the base.
Color: Moderate reddish orange [37. m.rO] when first removed, light yellowish brown [76. l.yBr] internally.
Pit wall: ¼" [6.4 mm.] thick.
Tendency to split: None observed.
Kernel:
*Form.*—Oval.
*Taste.*—Bitter.
*Viable.*—Yes.
*Average width.*—½" [12.7 mm.].
*Average length.*—¾" [19.1 mm.].
*Color.*—Pale yellow [89. p.Y] when first removed.
*Pellicle color.*—Moderate yellowish brown [77. m.yBr].
*Amygdalin:* Abundant.

USE

Market: Fresh and long distance shipping.
Keeping quality: Good.
Shipping quality: Good.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is most similar to its seed parent, the Spring Bright Nectarine (U.S. Plant Pat. No. 7,507) by producing fruit that is large in size, very firm in texture, and full red in skin color, but is distinguished therefrom and an improvement thereon by blooming 1 week later, by having reniform glands instead of globose, by having a bitter kernel instead of sweet, and by producing fruit that matures 7 days later and is subacidic in flavor instead of acidic.

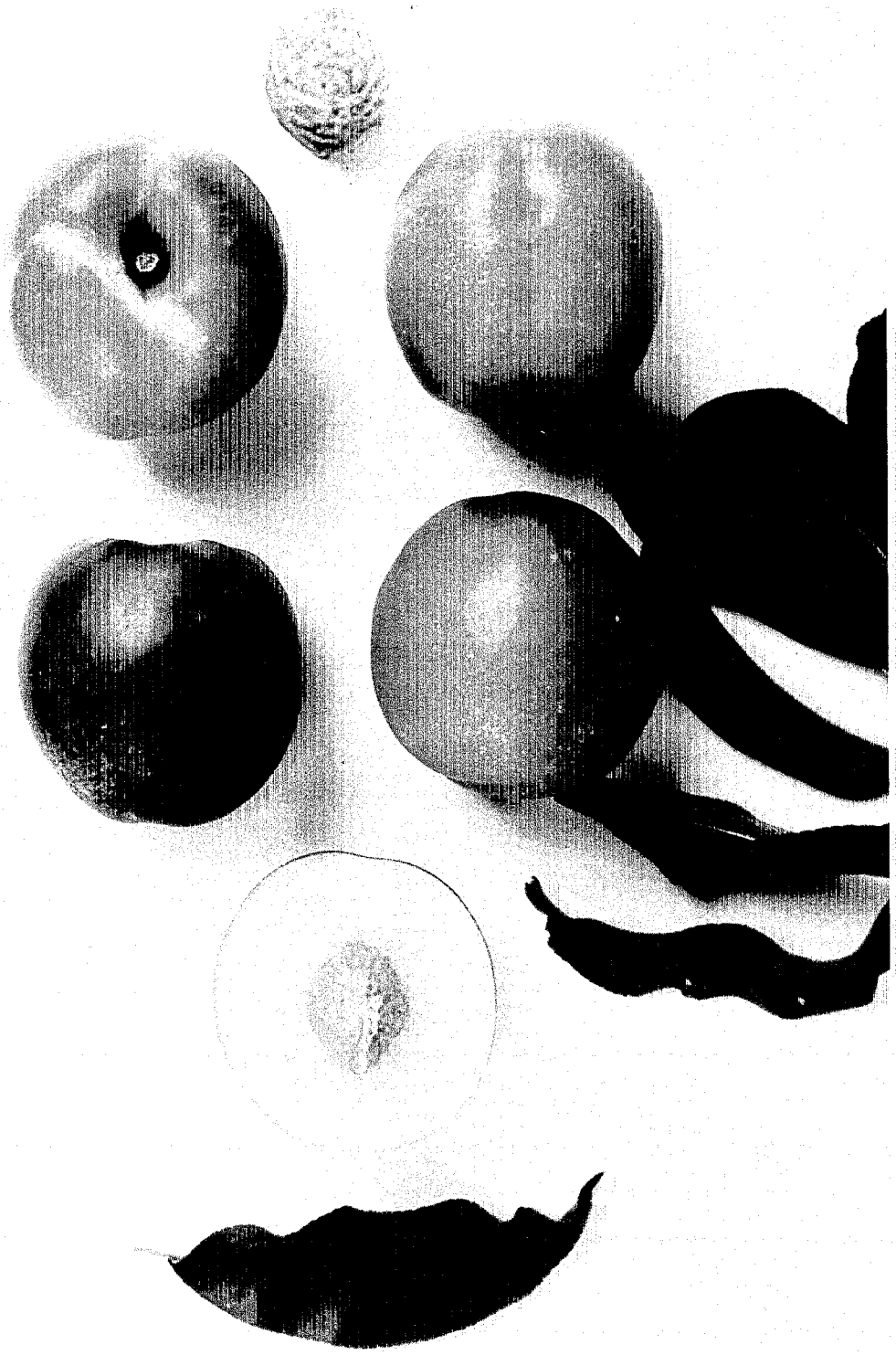

* * * * *